United States Patent [19]

Skog

[11] Patent Number: 6,000,397
[45] Date of Patent: Dec. 14, 1999

[54] METHOD AND DEVICE FOR DETECTING A VARIATION IN A FLOWING MEDIUM

[75] Inventor: Göran Skog, Bromma, Sweden

[73] Assignee: Siemens Elema AB, Solna, Sweden

[21] Appl. No.: 08/901,569

[22] Filed: Jul. 28, 1997

[30] Foreign Application Priority Data

Jul. 29, 1996 [SE] Sweden .................................. 9602886

[51] Int. Cl.[6] .................................................. A61M 16/00
[52] U.S. Cl. .............................. 128/204.22; 128/204.23; 128/203.12; 128/205.12; 600/532
[58] Field of Search ........................ 128/204.22, 204.21, 128/204.23, 910, 913, 914, 203.25, 203.12, 205.12; 600/532

[56] References Cited

U.S. PATENT DOCUMENTS

| | | |
|---|---|---|
| 4,062,373 | 12/1977 | Clark et al. .................................. 137/3 |
| 4,221,567 | 9/1980 | Clark et al. .............................. 600/532 |
| 4,619,269 | 10/1986 | Cutler et al. .............................. 600/532 |
| 4,799,374 | 1/1989 | Bossart et al. . |
| 5,109,850 | 5/1992 | Blanco et al. . |
| 5,325,861 | 7/1994 | Goulding ................................. 600/532 |

FOREIGN PATENT DOCUMENTS

0 405 583  1/1991  European Pat. Off. .

*Primary Examiner*—John G. Weiss
*Assistant Examiner*—V. Srivastava
*Attorney, Agent, or Firm*—Hill & Simpson

[57] ABSTRACT

In a method for detecting a variation, such as a variation in the concentration of a substance, in a flowing medium, a sample of the medium is made to flow past a sensor for detecting the variation, with the direction of flow of the sample being reversed and the velocity of the sample in relation to the sensor being reduced during passage of the sample through the sensor. A device for detecting such a variation contains a sensor and a pump controlled to reverse the direction of flow and to reduce the velocity of the sample of the medium for making a measurement of the sample.

10 Claims, 2 Drawing Sheets

METHOD AND DEVICE FOR DETECTING A VARIATION IN A FLOWING MEDIUM

BACKGROUND OF THE INVENTION

1. Field of the Invention

The present invention is directed to a method and device for detecting a variation, such as a variation in the concentration of a substance, in a flowing medium flowing at a flow velocity in a conduit of the type wherein a sample of the medium is with drawing from the conduit and is passed through a sensor at a velocity which is lower than the flow velocity, for detecting the variation.

2. Description of the Prior Art

The long response times of gas sensors is a major disadvantage in many applications. Sensor sluggishness can lead to distorted results in e.g. the measurement of variation, such as rapid changes in the concentration of a substance in a flowing medium. Thus, a sluggish sensor would cause change exhibiting a steep pulse slope to appear as if it had a more gradual slope. In the ventilator and anaesthesia field, such slow response time is a particular problem with oxygen sensors, but is also a problem with carbon dioxide sensors.

In an effort to avoid problems associated with sluggish sensors, special measurement methods of varying complexity must often be used. For example, European Application 0 392 503 describes a special technique for determining oxygen consumption and carbon dioxide output from breath to breath in a patient on a ventilator.

Another special measurement method is disclosed in U.S. Pat. No. 4,202,352, wherein exhaled gas from several breaths are stored in a gas storage tube. During analysis, the stored gas is passed through a gas analyzer at a reduced velocity (compared with the velocity of the exhaled gas).

One drawback with this method is the risk of diffusion of gas within the stored gas. In particular, the diffusion will be greatest within portions exhibiting rapid changes in concentration. There is also a risk that the gas analyzer tube itself will cause contamination of the gas. This happens because gas particles near the wall of the tube can have other flow characteristics than gas particles in the middle of the tube (e.g. laminar and turbulent flows have different characteristics).

SUMMARY OF THE INVENTION

An object of the present invention is to provide a technique for detecting a variation in a flowing medium which resolves the above problems in a simple fashion.

The above object is achieved in accordance with the principles of the present invention in a method and a device for detecting a variation in a medium flowing in a conduit, such as a variation in a concentration of a substance in the flowing medium, wherein a sample of the medium withdrawn from the conduit and is caused to flow past a sensor, for detecting the variation, with a velocity that is lower than the velocity of the flowing medium itself in the conduit, with the velocity at the sensor which is lower than the velocity of the medium in the conduit being produced by reversing the direction of flow of the sample before the sample interacts with the sensor.

When the flow direction of sample is reversed in relation to the sensor the latest drawn part of the sample will be analyzed first (with a lower velocity through the sensor). By controlling the sampling in an appropriate manner, the most interesting portions of the sample can be analyzed with no risk of diffusion or other contamination of the sample. If the sensor reproduces the variation in a generally accurate fashion, the exact variation can be subsequently electronically restored with the aid of an appropriate computer algorithm.

It should be noted that the above technique is suitable for use only if certain characteristics of the sample are of interest, because other information in the sample is lost.

According to an embodiment of the invention, the sample of the medium is pumped from the flowing medium with a higher velocity than the velocity of the flowing medium. This contributes to enhance the resolution of rapid changes.

In another embodiment of the device according to the invention, the sensor is disposed so as to measure the variation as the pump draws the sample from the flowing medium. This naturally only allows for a coarse analysis, however, the coarse analysis can be used for spotting the interesting parts of the sample, and thus can be used for controlling when to stop and reverse the flow with a lower velocity for conducting detailed analysis of the interesting part.

According to another embodiment of the inventive device, several sensors are arranged to measure the variation of one substance at several locations, or to measure the variation of several substances at one or several locations.

DESCRIPTION OF THE PREFERRED EMBODIMENTS

Figure 1:
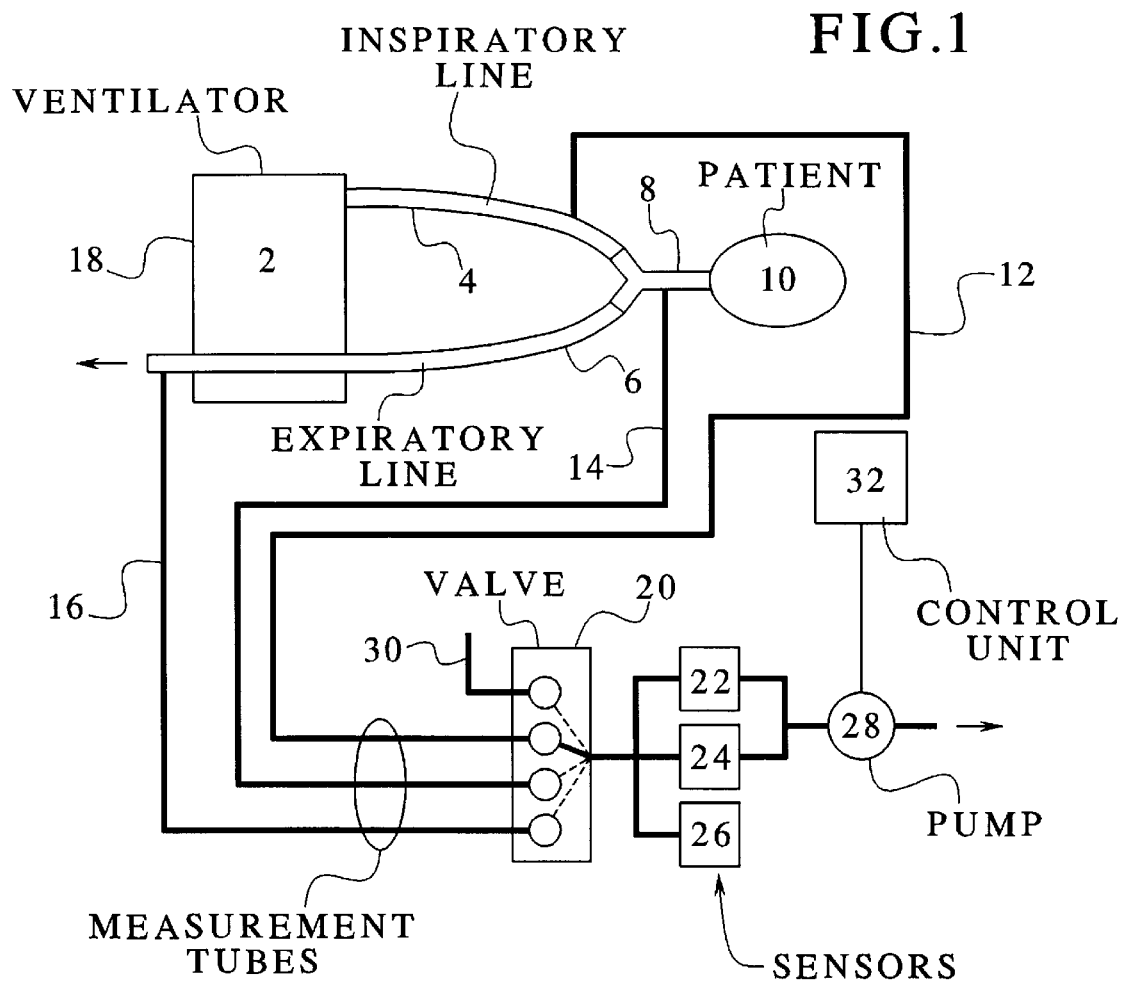
FIG. 1 illustrates the application of the technique according to the invention to a ventilator system.

FIG. 1 shows a ventilator system with 2 ventilator 2, connected to a patient 10 vis an inspiratory line 4, an expiratory line 6, and a Y-piece 8. Respiratory gas is supplied to and removed from the patient through the lines 4, 6 and 8. Also a first measurement tube 12 is connected to the inspiratory line 4, a second measurement tube 14 connected to the Y-piece 8 and, a third measurement tube 16 is connected to the expiratory line 6. The third measurement tube 18 is connected close to the outlet of the expiratory line 6 to ambient air. The measurement tubes 12, 14 and 16 can be selectively connected, via a multiplex valve 20, to sensors 22 and 24 and to pressure gauge 26 for analyzing the respiratory gas. These sensors 22 and 24 can be of an oxygen sensor 22 and a carbon dioxide sensor 24. A pump 28 is arranged to pump specimens or samples of inspiratory and expiratory gases through the measurement tubes 12, 14 and 16, via the multiplex valve 20, to the sensors 22 and 24 and pressure gauge 26 for analysis. The sensors 22, 24 can also be connected, via an additional tube 30 connected to the multiplex valve 20, to ambient air or to some other suitable location (as disclosed below). Likewise, the outlet of the pump 28 can be connected to ambient air or to some other suitable location.

The pumping rate of the pump 28 and its pumping direction are controlled by a control unit 32. In the embodiment of FIG. 1, the sensors 22 and 24 and pressure gauge 26 are situated at a distance from each measurement point (which are the respective connection points of the measurement tubes 12, 14 and 16 with the inspiratory line 4, the Y-piece 8 and the expiratory line 6). In order to achieve relatively short analysis times of samples, the pump 28 is controlled so as to draw a sample from the respective line at a fast rate (faster than the velocity therein of the respiratory gas itself) for transporting samples from the sampling site on the inspiratory line 4, expiratory line 6 and Y-piece 8 respectively to the sensors 22 and 24 and to the pressure gauge 26. This also enhances the resolution of rapid changes in respiratory gas. Pressures measured by the pressure gauge are corrected for tho influence of the measurement lines 12, 14 and 16 in known manner. When a sample has been pumped past the sensors 22 and 24 (and resides between the sensors 22 and 24 and the pump 28) the pumping direction is reversed and the rate (velocity) is reduced to a slower pumping rate so as to pump the sample past the sensors 22 and 24 in reversed direction.

This approach improves the ability of the sensors 22 and 24 to measure rapid variations or changes in the samples without a loss of information. If e.g., the steep leading front of a pulse is of interest, i.e. the pulse's rise time, and this pulse is pumped at "full" speed through a sensor, whose maximal rise time is much slower, the sensor will reproduce this leading front with a slope less steep than its true slope, and the measurement will accordingly be erroneous. As noted above, the problem of sensor sluggishness is greatest with oxygen sensors. If the velocity of the front past the sensor is slowed, however, the problem of a sluggish sensor can be reduced, and the samples signal can be subsequently electronically restored, with the aid of a suitable algorithm, to its original waveform (configuration).

Since the sample passes the sensors 22 and 24 when it passes toward the pump, the signal from the sensors 22 and 24 can be used (notwithstanding the sluggishness of the sensors 22 and 24) to indicate when the interesting part of the sample has passed the sensors 22 and 24. Upon such indication (e.g. a steep leading front), the pump 28 is stopped and reverse its pumping at a slower speed for detailed analysis of the interesting part of the sample. This also means that the most interesting part of the sample to analyze, will enter the sensors 22 and 24 first, thereby reducing diffusion and contamination of the sample. This will be explained further in connection with FIGS. 2 and 3 below.

The multiplex valve 20 can remain in the same state (allowing the sample to be pumped back toward the sample site) or can be switched to connect with a tube 30. If switched to connect with tube 30, the sample can be pumped into ambient air. The tube 30 can alternatively be connected to an evacuation system for collecting all samples, or can he connected to another part of the respiration lines (inspiratory line 4, expiratory line 6, Y-piece 8). The same is true for the outlet of the pump 28. This can also be connected to an evacuation system for collecting gas or to another part of the respiration lines (inspiratory line 4, expiratory line 8, Y-piece 8).

In general, the inventive method and device cause the direction of flow of the sample to be reversed and the velocity of the sample reduced in relation to the velocity at which the sample of the medium to be analyzed (in this case respiratory gas) is withdrawn.

In the system in FIG. 1, measurements of e.g. oxygen can be made in the inspiratory line 4, through the measurement tube 12, and in the expiratory line 6, through the measurement tube 16, for determining the oxygen consumption of the patient 10. The end tidal sample is taken from the Y-piece 8, through the measurement tube 14 in a known manner, for determining the carbon dioxide concentration.

Figure 2:
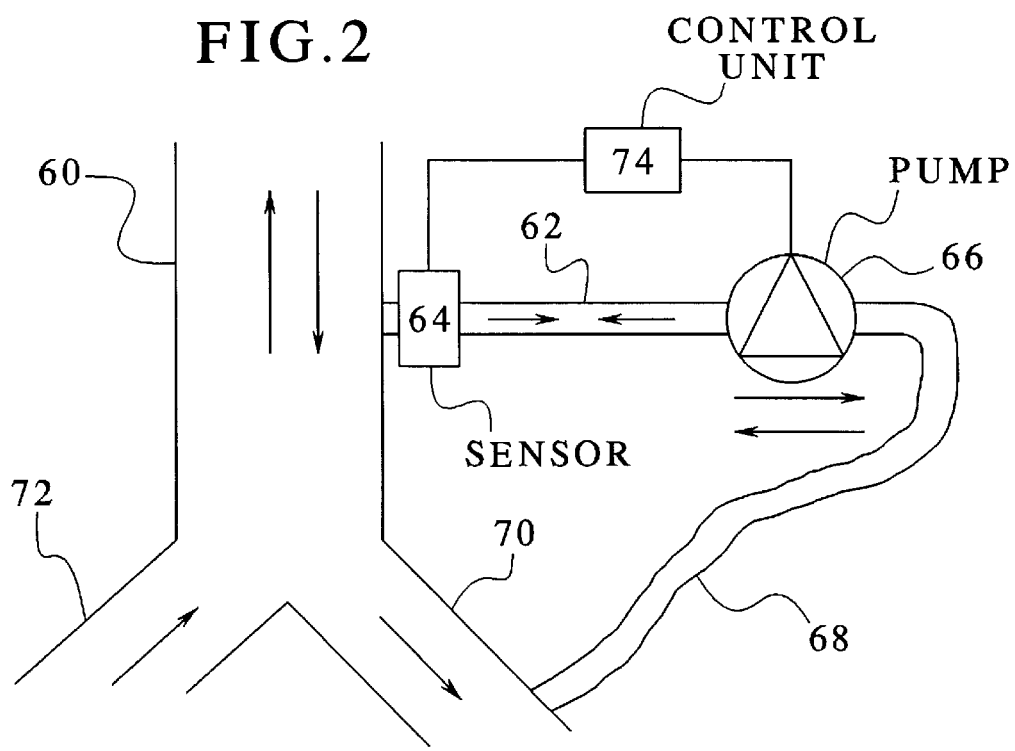
FIG. 2 shows a first suitable position for the sensor and pump for use with such a ventilator system.

FIG. 2 shows a Y-piece similar to the one in the ventilator system in FIG. 1. In this embodiment, however, a different approach to placement of sensors is disclosed. A branch tube 62 is connected to the Y-piece 60. A sensor 64 is arranged to analyze samples from the Y-piece 60 in the branch tube 62. Samples can be extracted from the main flow of respiratory gas through the Y-piece 60. With this location of the sensor 64, an analysis can be made almost immediately after the sample has been taken. A pump 66 is arranged to pump a sample from the Y-piece 60 and to reverse the flow (as indicated by the arrows) to pump the sample, at a slower rate, through the sensor 64 (for analysis) back to the Y-piece 60. If controlled accurately, the pump 66 could draw the precise volume to be analyzed, and return this to the Y-piece 60.

In the embodiment shown in FIG. 2, however, a return tube 68 from the pump 66 directs excess gas over to the expiratory side 70 (the inspiratory side being designated 72). (Similar to that described in connection with the embodiment of FIG. 1, such excess or surplus gas can be directed completely to ambient air or to an evacuation system.)

The sensor 64 is connected to a control unit 74 for the pump 66. As described above, a coarse analysis can be made as sample gas is drawn through the sensor 64 toward the pump 66 for identifying interesting parts of the sampled gas, whereupon the pump 66 is reversed and slowed for conducting a detailed analysis.

Figure 4:
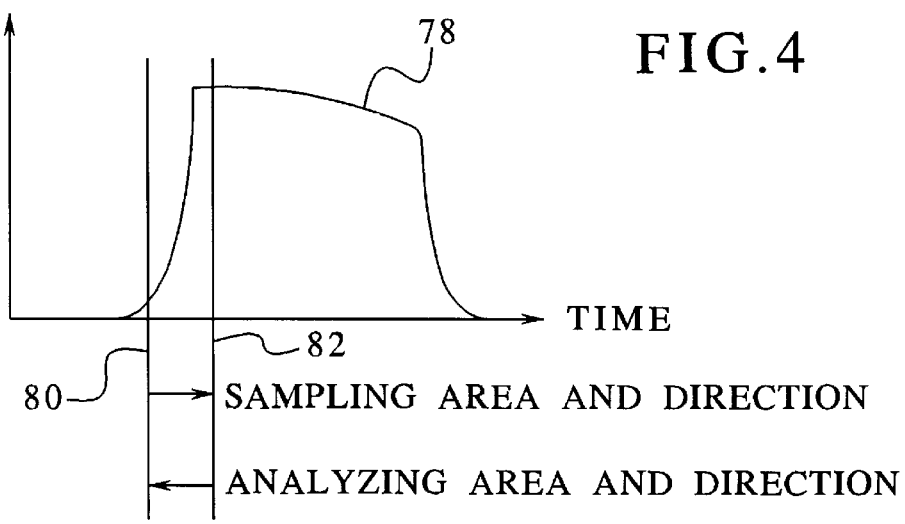
FIG. 4 schematically illustrates an advantageous effect of the method according to the invention.

One important advantage of this method is shown in the diagram in FIG. 4. The diagram shows concentration and time for a curve 78 (e.g. a $CO_2$-curve). The curve 78 includes two steep parts with rapid changes. A sampling area is indicated between two lines 80 and 82. An upper arrow shows the time-based sample direction, i.e., from zero to maximum concentration. When analyzing the sample with reversed flow, the time-based analyzing direction will be opposite, as indicated with the lower arrow, i.e., the steep rise will be analyzed from maximum toward minimum. Thus, the most interesting part of the sample (near the maximum) will be analyzed first, giving practically no time for diffusion of $CO_2$ to parts of the sample having lower concentration of $CO_2$. Since velocity is lower during analysis, the time frame for the analysis will be wider than indicated in the FIG.

Figure 3:
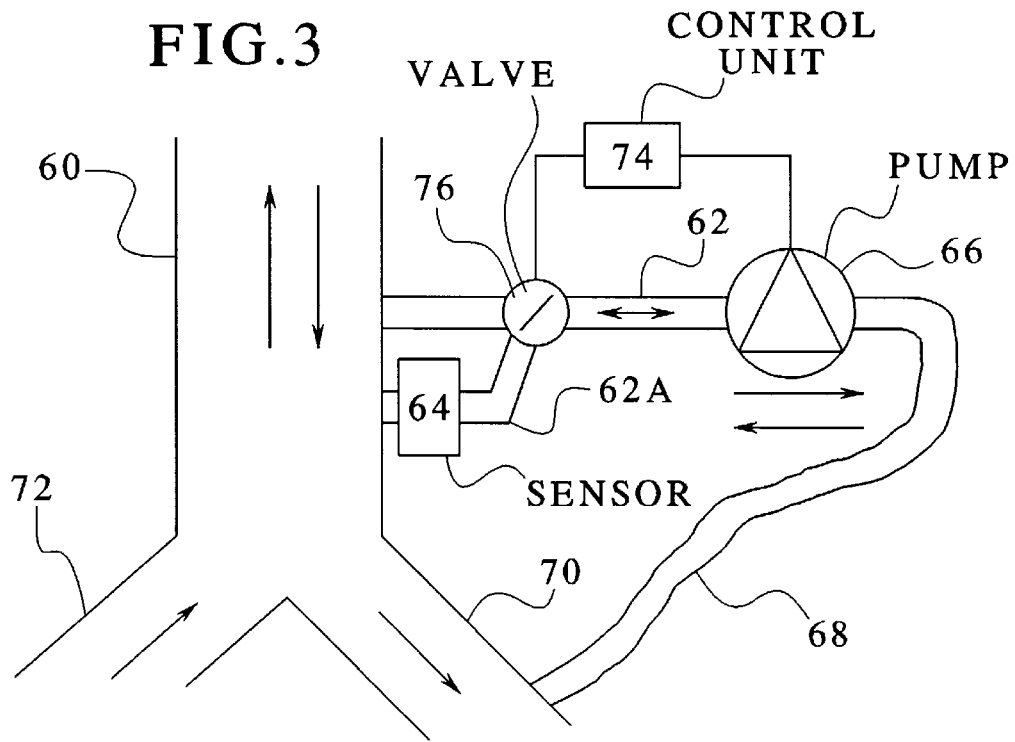
FIG. 3 shows a second suitable position for the sensor and pump for use with such a ventilator system.

FIG. 3 shows an alternative embodiment to that disclosed in FIG. 2. Components and elements that can be identical have the same reference numbers. The major difference in the embodiment of FIG. 3 compared to that of FIG. 2 is that in FIG. 3 the branch tube 62 has a separate return tube 62A, in which the sensor 62 is placed. When a sample is drawn from the Y-piece 60 through the branch tube 62 it will pass a valve 76, which is switched to conduct the sample to the return tube 62A when the pump 66 is reversed.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for measuring a concentration gradient of a gas in a medium containing said gas comprising:
    a conduit in which said medium containing said gas flows at a flow velocity;
    a measuring tube in fluid communication with said conduit;

a concentration gradient sensor disposed at a sensor location in fluid communication with said measuring tube;

a pump in fluid communication with said measuring tube; and control means for controlling said pump or causing said pump to withdraw a sample of said medium from said conduit at a velocity which is at least as high as said flow velocity and for subsequently reversing a flow direction of said sample in said measuring tube for causing said sample to flow past said sensor location at a velocity which is lower than said flow velocity, said sensor measuring said concentration gradient of said gas in said medium while said medium is flowing past said sensor location at said velocity which is lower than said flow velocity.

2. A device as claimed in claim 1 wherein said control means comprises means for controlling said pump for initially drawing said sample from said conduit through said sensor and for subsequently reversing said direction of flow of said sample and pumping said sample at least said velocity which is lower than said flow velocity, back through said sensor toward said flowing medium.

3. A device as claimed in claim 1 further comprising feedback means connecting said sensor and said control means for causing said control means to operate said pump to reverse the direction of flow of said sample dependent on a signal from said sensor.

4. A device as claimed in claim 1 wherein said control means comprises means for causing said pump to withdraw said sample from said conduit at a velocity that is higher than said flow velocity of said medium.

5. A device as claimed in claim 1 further comprising a plurality of sensors disposed at a plurality of different locations in said measuring tube for measuring a plurality of different concentration gradients in said sample, with said sample being caused to pass each of said plurality of sensors by said pump controlled by said control means.

6. A device as claimed in claim 1 further comprising a respiratory-assist device having an inspiratory line comprising said conduit in which said medium flows.

7. A device as claimed in claim 1 further comprising a respiratory-assist device having an expiratory line comprising said conduit in which said medium flows.

8. A method for measuring a concentration gradient of a gas in a medium containing said gas, said medium flowing in a conduit at a flow velocity, comprising the steps of:

withdrawing a sample of said medium from said conduit into a measuring tube, connected to said conduit, at a velocity which is at least as high as said flow velocity;

disposing a sensor in fluid communication with said measuring tube at a sensor location;

reversing a direction of flow of said sample in said measuring tube at least at said sensor location to cause said sample to flow past said sensor at a velocity which is lower than said flow velocity; and measuring the concentration gradient of said gas in said sample using said sensor at said sensor location while said sample is flowing at said velocity which is lower than said flow velocity.

9. A method as claimed in claim 8 wherein the step of withdrawing said sample comprises withdrawing said sample from said flowing medium at a velocity which is higher than said flow velocity of said medium in said conduit.

10. A method as claimed in claim 8 comprising the additional step of making a coarse measurement of said concentration gradient in said sample prior to reversing the direction of flow of said sample, and wherein the step of measuring the concentration gradient of said gas in said sample while said sample is flowing at said velocity which is lower than said flow velocity comprises making a detailed measurement, finer than said coarse measurement, of said concentration gradient.

* * * * *